(12) United States Patent
Ohtani et al.

(10) Patent No.: US 11,104,893 B2
(45) Date of Patent: Aug. 31, 2021

(54) KETOSE 3-EPIMERASE WITH IMPROVED THERMAL STABILITY

(71) Applicant: Matsutani Chemical Industry Co., Ltd., Itami (JP)

(72) Inventors: Kouhei Ohtani, Itami (JP); Kazuhiko Ishikawa, Itami (JP); Masako Nakamura, Itami (JP); Kazutaka Katsuki, Itami (JP)

(73) Assignee: MATSUTANI CHEMICAL INDUSTRY CO., LTD., Hyogo (JP)

( * ) Notice: Subject to any disclaimer, the term of this patent is extended or adjusted under 35 U.S.C. 154(b) by 0 days.

(21) Appl. No.: 16/962,114

(22) PCT Filed: Jan. 24, 2019

(86) PCT No.: PCT/JP2019/002340
§ 371 (c)(1),
(2) Date: Jul. 14, 2020

(87) PCT Pub. No.: WO2019/146717
PCT Pub. Date: Aug. 1, 2019

(65) Prior Publication Data
US 2020/0347377 A1 Nov. 5, 2020

(30) Foreign Application Priority Data

Jan. 24, 2018 (JP) .............................. JP2018-009389

(51) Int. Cl.
*C12N 9/90* (2006.01)
*C12N 15/00* (2006.01)
(Continued)

(52) U.S. Cl.
CPC ............... *C12N 9/90* (2013.01); *C12N 15/00* (2013.01); *C12P 19/02* (2013.01); *C12P 19/24* (2013.01); *C12Y 501/03* (2013.01)

(58) Field of Classification Search
CPC ....................................................... C12N 9/90
See application file for complete search history.

(56) References Cited

U.S. PATENT DOCUMENTS 9,932,617 B2 * 4/2018 Izumori .................. C12P 19/02
2010/0190225 A1 7/2010 Oh et al.
(Continued)

FOREIGN PATENT DOCUMENTS

CN 106350498 A 1/2017
JP 2008-541753 A 11/2008
(Continued)

OTHER PUBLICATIONS

Akihide Yoshihara, et al., "Purification and characterization of D-allulose 3-epimerase derived from Arthrobacter globiformis M30, a GRAS microorganism", Journal of Bioscience and Bioengineering, 2017, vol. 123, No. 2, pp. 170-176.
(Continued)

*Primary Examiner* — Yong D Pak
(74) *Attorney, Agent, or Firm* — Sughrue Mion, PLLC (57) ABSTRACT

It is found that a variant enzyme with an improved thermal stability can be obtained by substituting a specific amino acid in the amino acid sequence of a ketose 3-epimerase originated from *Arthrobacter globiformis* and that D-psicose can be efficiently produced.

4 Claims, 1 Drawing Sheet
Specification includes a Sequence Listing.

(51) Int. Cl.
  *C12P 19/02* (2006.01)
  *C12P 19/24* (2006.01)

(56) References Cited

U.S. PATENT DOCUMENTS

| | | | |
|---|---|---|---|
| 2014/0199732 | A1 | 7/2014 | Kim et al. |
| 2015/0344925 | A1 | 12/2015 | Izumori et al. |
| 2016/0152967 | A1 | 6/2016 | Cho et al. |
| 2016/0281076 | A1 | 9/2016 | Lanos et al. |
| 2018/0179510 | A1 | 6/2018 | Lanos et al. |

FOREIGN PATENT DOCUMENTS

| | | |
|---|---|---|
| JP | 2014-525244 A | 9/2014 |
| JP | 2016-518135 A | 6/2016 |
| JP | 2016-528925 A | 9/2016 |
| WO | 2014/109254 A1 | 7/2014 |
| WO | WO-2016191267 A1 * 12/2016 | .............. C12P 19/02 |

OTHER PUBLICATIONS

Jin-Geun Choi, et al., "Improvement in the Thermostability of D-Psicose 3-Epimerase from Agrobacterium tumefaciens by Random and Site-Directed Mutagenesis", Applied and Environmental Microbiology, Oct. 2011, vol. 77, No. 20, pp. 7316-7320.

Wenli Zhang, et al., "Improving the Thermostability and Catalytic Efficiency of the D-Psicose 3-Epimerase from Clostridium bolteae ATCC BAA-613 Using Site-Directed Mutagenesis", Journal of Agricultural and Food Chemistry, 2016, vol. 64, pp. 3386-3393.

International Search Report for PCT/JP2019/002340 dated Apr. 2, 2019 (PCT/ISA/210).

* cited by examiner

KETOSE 3-EPIMERASE WITH IMPROVED THERMAL STABILITY

CROSS REFERENCE TO RELATED APPLICATIONS

This application is a National Stage of International Application No. PCT/JP2019/002340 filed Jan. 24, 2019, claiming priority based on Japanese Patent Application No. 2018-009389 filed Jan. 24, 2018.

TECHNICAL FIELD

The present invention relates to a novel ketose 3-epimerase with an improved thermal stability and a method for producing the same.

BACKGROUND ART

D-psicose is known as one of rare sugars, which exist only in very small quantities in the nature. Since the sweetness of D-psicose is about 70% of that of sugar, D-psicose is utilized as a sweetener. D-psicose has a caloric value almost close to zero, is also known to have various physiological functions, such as suppression of an increase in the blood sugar level, and thus is attracting attention as a food ingredient having functionality. For these reasons, the need for an efficient and safe method for producing D-psicose is increasing in the food industry.

On the other hand, since D-psicose is an epimer of D-fructose, production methods that react D-psicose 3-epimerase with D-fructose have been established. For example, ketose 3-epimerase originated from *Arthrobacter globiformis* M30 (Patent Literature 1) and D-psicose 3-epimerase originated from *Agrobacterium tumefaciens* (Patent Literature 2) are disclosed. In addition, a psicose epimerase variant originated from *Agrobacterium tumefaciens* (Patent Literature 3) and D-psicose 3-epimerase variant originated from *Burkholderia* (Patent Literature 4) with improved thermal stability, by which denaturation of enzymes due to a temperature is suppressed to maintain the production efficiency, are utilized for production of D-psicose.

CITATION LIST

Patent Literatures

Patent Literature 1: WO 2014/109254
Patent Literature 2: JP-T-2008-541753
Patent Literature 3: JP-T-2016-518135
Patent Literature 4: CNA106350498

SUMMARY OF INVENTION

Problems to be Solved by the Invention

As described above, the methods for producing D-psicose by reacting enzymes such as D-psicose 3-epimerase have been devised in various manners; however, a method for producing an enzyme having an improved thermal stability that produces D-psicose originated from bacterial strains such as *Arthrobacter globiformis* which has been confirmed to be safe for foods has not been established yet. Moreover, there is a problem that although the optimum temperature of ketose 3-epimerase originated from *Arthrobacter globiformis* is 60 to 80° C. under a condition where magnesium ($Mg^{2+}$) exists, when reaction is conducted for a long period of time at a reaction temperature exceeding 50° C., the enzyme activity gradually decreases, so that the production of D-psicose decreases.

Means for Solution of the Problems

As a result of studying methods for producing D-psicose by reacting enzymes in various ways, the present inventors found that a variant enzyme with an improved thermal stability can be obtained by substituting a specific amino acid in the amino acid sequence of a ketose 3-epimerase originated from *Arthrobacter globiformis* and found that this makes it possible to efficiently produce D-psicose. More specifically, the present inventors found that it is possible to obtain a ketose 3-epimerase variant comprising: at least one amino acid mutation in an amino acid sequence of a wild-type ketose 3-epimerase originated from *Arthrobacter globiformis* and represented by SEQ ID NO: 1, wherein the ketose 3-epimerase variant has the feature: (1) a ratio of the activity of the variant enzyme at 70° C. (t70) to that at 50° C. (t50), t70/t50, is higher than that of the wild-type enzyme, or (2) a residual enzyme activity A of the variant enzyme at 50° C. after having been treated at 60° C. for 1 hour in 50 mM phosphate buffer (pH 8.0, containing 2 mM magnesium sulfate) suspension when an activity of untreated enzyme at 50° C. is set to 100, is higher than that of the wild-type ketose 3-epimerase.

Specifically, the present invention has been completed based on the above-described finding and comprises the following embodiments <1> to <9>.

<1> A ketose 3-epimerase variant comprising:

at least one amino acid mutation in the amino acid sequence of SEQ ID NO: 1, which is of a wild-type ketose 3-epimerase originated from *Arthrobacter globiformis*, wherein the ketose 3-epimerase variant has the following feature:

(1) a ratio of the activity of the variant enzyme at 70° C. (t70) to that at 50° C. (t50), t70/t50, is higher than that of the wild-type enzyme, or (2) a residual enzyme activity A of the variant enzyme at 50° C. after having been treated at 60° C. for 1 hour in 50 mM phosphate buffer (pH 8.0, containing 2 mM magnesium sulfate) suspension when an activity of untreated enzyme at 50° C. is set to 100, is higher than that of the wild-type ketose 3-epimerase.

<2> The ketose 3-epimerase variant according to <1>, wherein the T70/T50 is 1.0 or more.

<3> The ketose 3-epimerase variant according to <1> or <2>, wherein the residual enzyme activity A is 40 or more.

<4> The ketose 3-epimerase variant according to any one of <1> to <3>, wherein the at least one amino acid mutation in the amino acid sequence of the wild-type ketose 3-epimerase is amino acid substitution(s) at 1 to 10 positions.

<5> The ketose 3-epimerase variant according to <1>, wherein the at least one amino acid mutation in the amino acid sequence of the wild-type ketose 3-epimerase is present at any of the following positions as counted from an amino terminus of the amino acid sequence of SEQ ID NO: 1: 6, 14, 22, 26, 34, 67, 68, 69, 70, 75, 91, 95, 100, 101, 110, 122, 137, 144, 160, 173, 177, 181, 200, 203, 214, 222, 226, 237, 261, 270, 271, 275, 278, 281, and 289.

<6> A ketose 3-epimerase variant, wherein the ketose 3-epimerase variant is selected from variants having mutations at the following positions as counted from an amino terminus of an amino acid sequence of SEQ ID NO: 1.

| Ketose 3-epimerase Variant | Mutated Position as Counted From Amino Terminus of Amino Acid Sequence of SEQ ID NO: 1 |
|---|---|
| 1 | 144 |
| 2 | 137 and 173 |
| 3 | 26 |
| 4 | 214 |
| 5 | 14 |
| 6 | 122 |
| 7 | 271 and 278 |
| 8 | 67, 68, 69 and 70 |
| 9 | 22 |
| 10 | 160 and 289 |
| 11 | 160, 271, 278, and 289 |
| 12 | 22, 67, 68, 69, 70, 160, and 289 |
| 13 | 22, 67, 68, 69, 70, 160, 177, and 289 |
| 14 | 222 |
| 15 | 278 |
| 16 | 200 |
| 17 | 177, 181, and 203 |
| 18 | 160, 226, and 289 |
| 19 | 237 |
| 20 | 270 and 281 |
| 21 | 275 and 278 |
| 22 | 177, 200, 237, 275, and 278 |
| 23 | 75 |
| 24 | 100 and 101 |
| 25 | 261 |
| 26 | 75, 177, and 237 |
| 27 | 6 and 177 |
| 28 | 110 and 177 |
| 29 | 67, 69, and 70 |
| 30 | 22 and 34 |
| 31 | 91 |
| 32 | 95 |
| 33 | 137 |
| 34 | 270 |

<7> The ketose 3-epimerase variant according to <6>, wherein the ketose 3-epimerase variant is further selected from the following variants.

| Ketose 3-epimerase Variant | Mutation in Amino Acid Sequence of SEQ ID NO: 1 |
|---|---|
| PM3 | S144C |
| PM4 | S137C and N173C |
| PM5 | T26C |
| PM9 | L214P |
| PM12 | F14W |
| PM14 | L122Y |
| PM15 | L122W |
| PM17 | H271C and D278C |
| PM18 | S67P, D68A, A69D, and T70G |
| PM19 | S22T |
| PM23 | R160A and H289X1 (X1 = VSARHKP (SEQ ID NO: 2)) |
| PM26 | R160A, H271C, D278C, and H289X1 (X1 = VSARHKP (SEQ ID NO: 2)) |
| PM28 | S22T, S67P, D68A, A69D, T70G, R160A, and H289X1 (X1 = VSARHKP (SEQ ID NO: 2)) |
| PM29 | S22T, S67P, D68A, A69D, T70G, R160A, H177M, and H289X1 (X1 = VSARHKP (SEQ ID NO: 2)) |
| PM31 | D222H |
| PM32 | D278F |
| PM33 | A200L |
| PM36 | H177M, Y181F, and Y203Q |
| PM37 | R160A, H289X1 (X1 = VSARHKP (SEQ ID NO: 2)), and K226D |
| PM38 | V237I |
| PM39 | A200K |
| PM40 | A270C and T281C |
| PM41 | F275C and D278C |
| PM43 | H177M, A200K, V237I, F275C, and D278C |
| PM44 | E75P |
| PM45 | T100P and D101V |
| PM46 | L261M |
| PM48 | R160A and H289X2 (X2 = VSAR (SEQ ID NO: 3)) |
| PM51 | E75P, H177M, and V237I |
| PM55 | R160A and H289X3 (X3 = VSARHK (SEQ ID NO: 4)) |
| PM56 | H6Y and H177M |
| PM57 | M110W and H177M |
| PM58 | S67P, A69D, and T70G |
| PM59 | S22T and V34I |
| PM60 | D278L |
| PM61 | V237L |
| PM62 | V91I |
| PM63 | A95R |
| PM64 | S137K |
| PM65 | A270K |

<8> The ketose 3-epimerase variant according to <6>, wherein the ketose 3-epimerase variant is further selected from the following variants.

| Ketose 3-epimerase Variant | Mutation in Amino Acid Sequence of SEQ ID NO: 1 |
|---|---|
| PM4 | S137C and N173C |
| PM17 | H271C and D278C |
| PM18 | S67P, D68A, A69D, and T70G, |
| PM23 | R160A and H289X1 (X1 = VSARHKP (SEQ ID NO: 2)) |
| PM26 | R160A, H271C, D278C, and H289X1 (X1 = VSARHKP (SEQ ID NO: 2)) |
| PM29 | S22T, S67P, D68A, A69D, T70G, R160A, H177M, and H289X1 (X1 = VSARHKP (SEQ ID NO: 2)) |
| PM32 | D278F |
| PM33 | A200L |
| PM38 | V237I |
| PM39 | A200K |
| PM41 | F275C and D278C |
| PM43 | H177M, A200K, V237I, F275C, and D278C |
| PM44 | E75P |
| PM45 | T100P and D101V |
| PM48 | R160A and H289X2 (X2 = VSAR (SEQ ID NO: 3)) |
| PM51 | E75P, H177M, and V237I |
| PM55 | R160A and H289X3 (X3 = VSARHK (SEQ ID NO: 4)) |
| PM57 | M110W and H177M |
| PM58 | S67P, A69D, and T70G |
| PM60 | D278L |
| PM61 | V237L |
| PM63 | A95R |
| PM65 | A270K |

<9> The ketose 3-epimerase variant according to any one of <1> to <8>, which is immobilized on an immobilization carrier.

<10> A method for producing D-psicose comprising: reacting the ketose 3-epimerase variant according to any one of <1> to <8> or the immobilized ketose 3-epimerase variant according to <9> with D-fructose.

Advantageous Effects of Invention

The present invention is capable of providing a ketose 3-epimerase variant which has an improved thermal stability as compared with the wild type and which is a production enzyme for a D-psicose originated from *Arthrobacter globiformis* which has been confirmed to be safe for foods.

Since the ketose 3-epimerase enzyme variant with an improved thermal stability originated from *Arthrobacter globiformis*, of the present invention is capable of maintaining the enzyme activity at a temperature higher than 50° C. for a relatively long period of time, it is possible to efficiently produce D-psicose as compared with the conventional ketose 3-epimerase (wild type) originated from *Arthrobacter globiformis* by reacting the ketose 3-epimerase enzyme variant with D-fructose which is a substrate.

DESCRIPTION OF EMBODIMENTS (*Arthrobacter Globiformis*)

The wild-type enzyme of ketose 3-epimerase utilized in the present invention is originated from *Arthrobacter globiformis*. In the food industry, the safety of *Arthrobacter globiformis* has been confirmed. In the United States, this is listed as "Glucose isomerase from immobilized *Arthrobacter globiformis*" in the EAFUS (Everything Added to Food in the United States): a food additive database of FDA. The usage of this bacterium is such that the bacterial cells are immobilized as they are, which proves that the safety of the bacterial cells themselves is very high.

In addition, in Europe, "Inventory of Microorganisms with a documented history of use in food" written by EFFCA (The European food&feed cultures association) and IFD (International Federation for the Roofing Trade) states that this is used for "Citrus fermentation to remove limonin and reduce bitterness". This indicates that like yeast and the like, this bacterial strain is used for fermentation, which in turn indicates that this bacterial strain has a considerably high safety.

In Japan, the genus *Arthrobacter* is listed in the Food Additive List as a microorganism from which enzymes such as "α-amylase, isomaltodextrase" are originated.

As described above, the genus *Arthrobacter* has a long history of usage in Japan, United States, and Europe, and can be said to be a bacterial strain with a high safety.

(Ketose 3-epimerase)

(1) The wild-type ketose 3-epimerase used in the present invention is originated from *Arthrobacter globiformis*, preferably originated from *Arthrobacter globiformis* M30 (accession number NITE BP-1111), and has the following amino acid sequence (SEQ ID NO: 1).

In addition, the wild-type ketose 3-epimerase of the present invention preferably is a ketose 3-epimerase that has the following (A) and (B) substrate specificities and has the following (a) to (f) physicochemical properties.

Substrate Specificities of Wild-type Ketose 3-epimerase:

(A) The wild-type ketose 3-epimerase epimerizes position 3 of a D- or L-ketose to generate a corresponding D- or L-ketose (B) The wild-type ketose 3-epimerase has the highest substrate specificities for a D-fructose and a D-psicose among D- or L-ketoses Physicochemical Properties of Wild-type Ketose 3-epimerase:

(a) Molecular Weight

The wild-type ketose 3-epimerase has a homotetrameric structure whose subunit has a molecular weight of 32 kDa, in which the molecular weight of the subunit measured by the SDS-PAGE is about 32 kDa and the molecular weight thereof measured by the gel filtration is 120 kDa.

(b) Optimum pH

The optimum pH of the wild-type ketose 3-epimerase is 6 to 11 under the condition of the presence of 20 mM of magnesium ($Mg^{2+}$) in the reaction at 30° C. for 30 minutes.

(c) Optimum Temperature

The optimum temperature of the wild-type ketose 3-epimerase is 60 to 80° C. under the condition of the presence of 20 mM of magnesium ($Mg^{2+}$) in the reaction at pH 7.5 for 30 minutes.

(d) pH Stability

The wild-type ketose 3-epimerase is stable at least at a pH within the range from 5 to 11 under the condition of being held at 4° C. for 24 hours.

(e) Thermal Stability

The wild-type ketose 3-epimerase is stable at about 50° C. or less under the condition of the presence of 4 mM of magnesium ion ($Mg^{2+}$), and is stable at about 40° C. or less under the condition of the absence of magnesium ion ($Mg^{2+}$), at pH 7.5 when being held for 1 hour.

(f) Activation by Metal Ions

The wild-type ketose 3-epimerase is activated by divalent manganese ions ($Mn^{2+}$), divalent cobalt ions ($Co^{2+}$), calcium ($Ca^{2+}$), and magnesium ions ($Mg^{2+}$).

(Ketose 3-Epimerase Variant)

The ketose 3-epimerase variant of the present invention is a variant that comprises at least one amino acid mutation in the amino acid sequence of a wild-type ketose 3-epimerase originated from *Arthrobacter globiformis* and represented by SEQ ID NO: 1, wherein the ketose 3-epimerase variant has the feature: (1) a ratio of the activity of the variant enzyme at 70° C. (t70) to that at 50° C. (t50), t70/t50, is higher than that of the wild-type enzyme, or (2) a residual enzyme activity A of the variant enzyme at 50° C. after having been treated at 60° C. for 1 hour in 50 mM phosphate buffer (pH 8.0, containing 2 mM magnesium sulfate) suspension when an activity of untreated enzyme at 50° C. is set to 100, is higher than that of the wild-type ketose 3-epimerase

```
                                                          (SEQ ID NO: 1)
  1 MKIGCHGLVW  TGHFDAEGIR  YSVQKTREAG  FDLVEFPLMD  PFSFDVQTAK

51 SALAEHGLAA  SASLGLSDAT  DVSSEDPAVV  KAGEELLNRA  VDVLAELGAT

101 DFCGVIYSAM  KKYMEPATAA  GLANSKAAVG  RVADRASDLG  INVSLEVVNR

151 YETNVLNTGR  QALAYLEELN  RPNLGIHLDT  YHMNIEESDM  FSPILDTAEA

201 LRYVHIGESH  RGYLGTGSVD  FDTFFKALGR  IGYDGPVVFE  SFSSSVVAPD

251 LSRMLGIWRN  LWADNEELGA  HANAFIRDKL  TAIKTIELH
```

The variant-type ketose 3-epimerase of the present invention is obtained based on the amino acid sequence of the wild-type ketose 3-epimerase by substituting (mutating) part of the amino acid sequence with a specific amino acid sequence.

Enzyme variants were obtained by substituting amino acids at various positions shown in Table 1, and whether the thermal stability was actually improved was tested for each variant.

As a result, variants that each comprises at least one amino acid mutation in the amino acid sequence of the wild-type ketose 3-epimerase originated from *Arthrobacter globiformis* and represented by SEQ ID NO: 1, wherein the ketose 3-epimerase variant has the feature: (1) a ratio of the activity of the variant enzyme at 70° C. (t70) to that at 50° C. (t50), t70/t50, is higher than that of the wild-type enzyme, or (2) a residual enzyme activity A of the variant enzyme at 50° C. after having been treated at 60° C. for 1 hour in 50 mM phosphate buffer (pH 8.0, containing 2 mM magnesium sulfate) suspension when an activity of untreated enzyme at 50° C. is set to 100, is higher than that of the wild-type ketose 3-epimerase.

(1) For the ratio of the enzyme activity (T70) at 70° C. to the enzyme activity (T50) at 50° C., T70/T50, the epimerase activity can be obtained, for example, by reacting the ketose 3-epimerase at 50° C. or 70° C. for 10 minutes using D-psicose (50 mM phosphoric acid buffer (pH 8.0) solution containing 2 mM $Mg_2SO_4$) as a substrate and measuring D-fructose, which is a reaction product. More specifically, after the reaction is stopped, the reaction liquid is loaded to HPLC, and the enzyme activity can be calculated from the peak area ratio between D-psicose, which is the substrate, and D-fructose, which is the reaction product, at 50° C. and 70° C. T70/T50 of the above-described variant-type ketose 3-epimerase thus calculated is preferably 0.70 or more, more preferably 0.80 or more, further preferably 1.0 or more, and still further preferably 1.5 or more.

(2) a residual enzyme activity A of the variant enzyme at 50° C. after having been treated at 60° C. for 1 hour in 50 mM phosphate buffer (pH 8.0, containing 2 mM magnesium sulfate) suspension when an activity of untreated enzyme at 50° C. is set to 100 can be obtained, for example, by treating the enzyme at 60° C. for 1 hour in the 50 mM phosphoric acid buffer (pH 8.0, containing 2 mM magnesium sulfate) suspension, thereafter reacting the treated enzyme at 50° C. for 10 minutes using D-psicose as a substrate, and measuring the epimerase activity. More specifically, after the reaction is stopped, the reaction liquid is loaded to HPLC, and the enzyme activities of the untreated enzyme and the enzyme treated at 60° C. for 1 hour can be calculated from the peak area ratio between D-psicose, which is the substrate, and D-fructose, which is the reaction product.

In the case where the enzyme activity of the wild-type ketose 3-epimerase represented by SEQ ID NO: 1 is set to 100, the residual enzyme activity A of the above-described variant-type ketose 3-epimerase is preferably 40 or more, more preferably 50 or more, further preferably 60 or more, and still further preferably 70 or more.

Although the at least one amino acid mutation in the amino acid sequence of the wild-type ketose 3-epimerase originated from *Arthrobacter globiformis* and represented by SEQ ID NO: 1 may be at least one mutation as long as the above-described activity is exhibited, but furthermore, the at least one amino acid mutation is preferably amino acid substitution(s) at 1 to 10 positions, and more preferably amino acid substitution(s) at 1 to 8 positions.

Moreover, the at least one amino acid mutation in the amino acid sequence of the wild-type ketose 3-epimerase is preferably present at any of the following positions as counted from the amino terminus of the amino acid sequence of SEQ ID NO: 1:

Positions: 6, 14, 22, 26, 34, 67, 68, 69, 70, 75, 91, 95, 100, 101, 110, 122, 137, 144, 160, 173, 177, 181, 200, 203, 214, 222, 226, 237, 261, 270, 271, 275, 278, 281, and 289.

Furthermore, the at least one amino acid mutation in the amino acid sequence of the wild-type ketose 3-epimerase is more preferably present at any of the following positions as counted from the amino terminus of the amino acid sequence of SEQ ID NO: 1:

Positions: 6, 14, 22, 26, 34, 67, 68, 69, 70, 75, 91, 95, 100, 101, 110, 122, 137, 144, 160, 173, 177, 200, 214, 222, 237, 261, 270, 271, 275, 278, 281, and 289.

The type of the amino acid inserted at each position by the substitution may be any amino acid as long as the T70/T50 or the residual enzyme activity A as described above is satisfied. Normally, it is preferable to substitute one amino acid with another amino acid, but at a carboxy terminus, one amino acid may be substituted with 1 to 10 continuous amino acids.

It is more preferable that the ketose 3-epimerase variant be selected from variants having amino acid substitutions at the following positions.

| Ketose 3-epimerase variant | Mutated Position as Counted From Amino Terminus of Amino Acid Sequence of SEQ ID NO: 1 |
|---|---|
| 1 | 144 |
| 2 | 137 and 173 |
| 3 | 26 |
| 4 | 214 |
| 5 | 14 |
| 6 | 122 |
| 7 | 271 and 278 |
| 8 | 67, 68, 69 and 70 |
| 9 | 22 |
| 10 | 160 and 289 |
| 11 | 160, 271, 278, and 289 |
| 12 | 22, 67, 68, 69, 70, 160, and 289 |
| 13 | 22, 67, 68, 69, 70, 160, 177, and 289 |
| 14 | 222 |
| 15 | 278 |
| 16 | 200 |
| 17 | 177, 181, and 203 |
| 18 | 160, 226, and 289 |
| 19 | 237 |
| 20 | 270 and 281 |
| 21 | 275 and 278 |
| 22 | 177, 200, 237, 275, and 278 |
| 23 | 75 |
| 24 | 100 and 101 |
| 25 | 261 |
| 26 | 75, 177, and 237 |
| 27 | 6 and 177 |
| 28 | 110 and 177 |
| 29 | 67, 69, and 70 |
| 30 | 22 and 34 |
| 31 | 91 |
| 32 | 95 |
| 33 | 137 |
| 34 | 270 |

It is further preferable that the ketose 3-epimerase variant be selected from variants having amino acid substitutions at the following positions.

| Ketose 3-epimerase variant | Mutated Position as Counted From Amino Terminus of Amino Acid Sequence of SEQ ID NO: 1 |
|---|---|
| 1 | 144 |
| 2 | 137 and 173 |
| 5 | 14 |
| 7 | 271 and 278 |
| 8 | 67, 68, 69 and 70 |
| 10 | 160 and 289 |
| 11 | 160, 271, 278, and 289 |
| 12 | 22, 67, 68, 69, 70, 160, and 289 |
| 13 | 22, 67, 68, 69, 70, 160, 177, and 289 |
| 15 | 278 |
| 16 | 200 |
| 19 | 237 |
| 21 | 275 and 278 |
| 22 | 177, 200, 237, 275, and 278 |
| 23 | 75 |
| 24 | 100 and 101 |
| 26 | 75, 177, and 237 |
| 27 | 6 and 177 |
| 28 | 110 and 177 |
| 29 | 67, 69, and 70 |
| 30 | 22 and 34 |
| 31 | 91 |
| 32 | 95 |
| 33 | 137 |
| 34 | 270 |

Still further preferably, the variants that exhibited improved thermal stability relative to the wild type have the following amino acid substitutions. In the Specification, for example, R160A indicates that arginine (R) in position 160 from the amino terminus in SEQ ID NO: 1 is substituted with alanine (A). H289VSARHKP indicates that the histidine (H) in position 289 from the amino terminus in SEQ ID NO: 1 is substituted with the sequence of VSARHKP (SEQ ID NO: 2).

| Ketose 3-epimerase variant | Mutation in Amino Acid Sequence of SEQ ID NO: 1 |
|---|---|
| PM3 | S144C |
| PM4 | S137C and N173C |
| PM5 | T26C |
| PM9 | L214P |
| PM12 | F14W |
| PM14 | L122Y |
| PM15 | L122W |
| PM17 | H271C and D278C |
| PM18 | S67P, D68A, A69D, and T70G |
| PM19 | S22T |
| PM23 | R160A and H289X1 (X1 = VSARHKP (SEQ ID NO: 2)) |
| PM26 | R160A, H271C, D278C, and H289X1 (X1 = VSARHKP (SEQ ID NO: 2)) |
| PM28 | S22T, S67P, D68A, A69D, T70G, R160A, and H289Z1 (X1 = VSARHKP (SEQ ID NO: 2)) |
| PM29 | S22T, S67P, D68A, A69D, T70G, R160A, H177M, and H289X1 (X1 = VSARHKP (SEQ ID NO: 2)) |
| PM31 | D222H |
| PM32 | D278F |
| PM33 | A200L |
| PM36 | H177M, Y181F, and Y203Q |
| PM37 | R160A, H289X1 (X1 = VSARHKP (SEQ ID NO: 2)), and K226D |
| PM38 | V237I |
| PM39 | A200K |
| PM40 | A270C and T281C |
| PM41 | F275C and D278C |
| PM43 | H177M, A200K, V237I, F275C, and D278C |
| PM44 | E75P |
| PM45 | T100P and D101V |
| PM46 | L261M |
| PM48 | R160A and H289X2 (X2 = VSAR (SEQ ID NO: 3)) |
| PM51 | E75P, H177M, and V237I |
| PM55 | R160A and H289X3 (X3 = VSARHK (SEQ ID NO: 4)) |
| PM56 | H6Y and H177M |
| PM57 | M110W and H177M |
| PM58 | S67P, A69D, and T70G |
| PM59 | S22T and V34I |
| PM60 | D278L |
| PM61 | V237L |
| PM62 | V91I |
| PM63 | A95R |
| PM64 | S137K |
| PM65 | A270K |

Among the above-listed variants, further preferable ketose 3-epimerase variants are PM3, PM4, PM5, PM9, PM12, PM14, PM17, PM18, PM19, PM23, PM26, PM28, PM29, PM31, PM32, PM33, PM38, PM39, PM41, PM43, PM44, PM45, PM46, PM48, PM51, PM55, PM56, PM57, PM58, PM59, PM60, PM61, PM62, PM63, PM64, and PM65.

Among the above-listed variants, even more preferable ketose 3-epimerase variants are PM4, PM17, PM18, PM23, PM26, PM29, PM32, PM33, PM38, PM39, PM41, PM43, PM44, PM45, PM48, PM51, PM55, PM57, PM58, PM60, PM61, PM63, and PM65.

Among the above-listed variants, PM17, PM23, PM26, PM29, PM32, PM38, PM39, PM41, PM43, PM51, PM57, PM60, PM61, and PM65 are particularly preferable.

The ketose 3-epimerase variant of the present invention can be obtained by substitution appropriately using a publicly-known method at any position of at least one amino acid in the amino acid sequence of the wild-type ketose 3-epimerase (more specifically, at least one amino acid in the amino acid sequence of SEQ ID NO: 1). For example, a variant subjected to amino acid substitution at a target position can be obtained by a publicly-known genetic engineering approach.

In addition, the ketose 3-epimerase variant of the present invention can be produced, for example, by incorporating into a plasmid vector a nucleic acid sequence encoding an amino acid sequence of each variant, or a DNA fragment into which a ketose 3-epimerase mutation has been introduced followed by transforming *Escherichia coli* (host) or the like with the plasmid vector to thus prepare a desired transformant. The type of the recombinant vector to be used is not particularly limited, and may be a vector normally used in the art. Moreover, as the recombinant for producing the ketose 3-epimerase, *Escherichia coli, bacillus*, yeast, or *agrobacterium* may be used.

For the ketose 3-epimerase variant of the present invention, a crude enzyme or a purified enzyme may be used as an enzyme solution, but may be made into and used as an immobilized enzyme utilizing a publicly-known immobilization method, for example, the carrier binding method, the cross-linking method, the gel entrapment method, or the like.

In the case where the carrier binding method is utilized, a publicly-known immobilization carrier, for example, an ion-exchange resin, a synthesized adsorbent, activated carbon, porous glass, or silica gel may be used. In the case where an ion-exchange resin is used as the immobilization carrier, for example, a phenol-based gel weak-base ion-exchange resin or a styrene-based macroporous weak-base ion-exchange resin may be used. In the present invention, commercial products of these ion-exchange resins may be used, and commercial products of the phenol-based gel weak-base ion-exchange resins include DUOLITE™ A561, DUOLITE™ A568, DUOLITE™ PWA7 (which are manufactured by DowDuPont), and the like. In addition, commercial products of the styrene-based macroporous weak-base ion-exchange resin include AMBERLITE™ FPA95, AMBERLITE™ IRA904, AMBERLITE™ XE583 (each manufactured by DowDuPont), PUROLITE™ A111S, PUROLITE™ A103S (each manufactured by Purolite), DIAION™ WA20, DIAION™ WA30 (each manufactured by Mitsubishi Chemical Corporation), and the like.

By using the ketose 3-epimerase variant of the present invention or the immobilized ketose 3-epimerase variant of the present invention, it is possible to efficiently produce D-psicose.

More specifically, for example, when the immobilized ketose 3-epimerase variant of the present invention is used, it is possible to produce a high-purity D-psicose aqueous solution by continuously passing a D-fructose aqueous solution through a reactor column packed with the immobilized ketose 3-epimerase variant to obtain a mixed aqueous solution of D-fructose and D-psicose in which part of D-fructose is converted into D-psicose, and thereafter performing decolorization—desalination—chromatographic fractionation by publicly-known methods. Furthermore, after that, crystal D-psicose can also be produced by a publicly-known method.

When the D-fructose aqueous solution is passed through the reactor column, the D-fructose aqueous solution is desirably heated to 50 to 80° C., desirably has a concentration of 30 to 70 wt %, and is desirably adjusted to pH 6 to 9 by a pH adjuster such as caustic soda. In addition, the flow speed when the D-fructose aqueous solution is passed through the reactor column is desirably adjusted such that the conversion rate from D-fructose to D-psicose is 20% or more, which is close to the reaction equilibrium of the enzyme. In addition, various ions, for example, 10 to 100 ppm of magnesium ions and 50 to 500 ppm of sulfurous acid ions may be contained as an activator and a stabilizer for the enzyme.

Hereinafter, the present invention is described in further detail using Examples; however the content of the present invention is not limited to these Examples.

EXAMPLES

<Selection of Portions to be Substituted in Amino Acid Sequence of Ketose 3-Epimerase>

First, in order to select amino acid sequences related to the activity and the thermal stability of the ketose 3-epimerase, primary structures (amino acid sequences) having high homology with the ketose 3-epimerase originated from this strain are searched for by Blast. As a result, primary structure information on 12 enzymes having high homology with the ketose 3-epimerase was obtained. Since the conformation of the enzyme originated from this strain is not determined, information on this is not available. In view of this, enzymes whose conformations have been revealed were selected from the above-described 12 enzymes, and the estimated conformation model of the target enzyme was constructed using the SWISS-MODEL and the energy minimization calculation. By comparing this model conformation with the structure of a similar enzyme, portions that contribute to the structural stability in this enzyme are searched for and selected, and substitution of amino acids that were considered physicochemically to be able to thermally stabilize the conformation of the enzyme was conducted.

As positions of specific amino acid sequences expected to improve the thermal stability, positions shown in Table 1 were selected to be substituted with specific amino acid sequences.

As the conversion into specific amino acid sequences, for example, substitution with amino acid sequences which were expected to be effective in improvement in hydrophobic interaction, stabilization of the loop structures of the peptide main chains, introduction of covalent bond between amino acids by disulfide bonding, improvement in space density, and stabilization of assembly attributable to extension of the protein C-terminus was made (Table 1).

TABLE 1

| Ketose 3-epimerase variant | Mutation in Amino Acid Sequence of SEQ ID NO: 1 |
|---|---|
| PM3 | S144C |
| PM4 | S137C and N173C |
| PM5 | T26C |
| PM9 | L214P |
| PM12 | F14W |
| PM14 | L122Y |
| PM15 | L122W |
| PM17 | H271C and D278C |
| PM18 | S67P, D68A, A69D, and T70G |
| PM19 | S22T |
| PM23 | R160A and H289X1 (X1 = VSARHKP (SEQ ID NO: 2)) |
| PM26 | R160A, H271C, D278C, and H289X1 (X1 = VSARHKP (SEQ ID NO: 2)) |
| PM28 | S22T, S67P, D68A, A69D, T70G, R160A, and H289X2 (X2 = VSARHKP (SEQ ID NO: 2)) |
| PM29 | S22T, S67P, D68A, A69D, T70G, R160A, H177M, and H289X2 (X2 = VSARHKP (SEQ ID NO: 2)) |
| PM31 | D222H |
| PM32 | D278F |
| PM33 | A200L |
| PM36 | H177M, Y181F, and Y203Q |
| PM37 | R160A, H289X2 (X2 = VSARHKP (SEQ ID NO:2)), and K226D |
| PM38 | V237I |
| PM39 | A200K |
| PM40 | A270C and T281C |
| PM41 | F275C and D278C |
| PM43 | H177M, A200K, V237I, F275C, and D278C |
| PM44 | E75P |
| PM45 | T100P and D101V |
| PM46 | L261M |
| PM48 | R160A and H289X2 (X2 = VSAR (SEQ ID NO: 3)) |
| PM51 | E75P, H177M, and V237I |
| PM55 | R160A and H289X3 (X3 = VSARHK (SEQ ID NO: 4)) |
| PM56 | H6Y and H177M |
| PM57 | M110W and H177M |
| PM58 | S67P, A69D, T70G |
| PM59 | S22T and V34I |
| PM60 | D278L |
| PM61 | V237L |
| PM62 | V91I |
| PM63 | A95R |
| PM64 | S137K |
| PM65 | A270K |

<Creation of Expression Vectors and Transformation of *Escherichia coli*>

First, mutation was conducted by the PCR method or the gene synthesis service (Thermo Fisher Scientific) based on DNA of ketose 3-epimerase containing 1 or 2 or more substituted amino acid sequences described in Table 1. The DNA fragments subjected to mutagenesis were incorporated into the pQE60 (Qiagen) vector for expressing *Escherichia coli* to transform *Escherichia coli* (host). The mutated sites were confirmed by a sequence analysis.

<Preparation of Crude Enzyme Solution>

First, a transformant (*Escherichia coli*) that expresses the ketose 3-epimerase variant enzyme was planted into an LB growth medium (culture solution) containing 100 μg/ml of ampicillin and 50 μg/ml of kanamycin and was precultured at 37° C. for 16 hour. This preculture solution was added to a 10- to 100-fold volume of a main culture solution containing 0.1 mM IPTG and was cultured at 20° C. for 24 hours to derive the target enzyme expression. Next, the main culture solution was centrifuged at 4° C. and 5,500×g for 20 minutes with a centrifuge. After the centrifugation, the supernatant was removed and the bacterial cells were collected. The collected bacterial cells were suspended in an appropriate amount of 50 mM phosphoric acid buffer (pH 8.0, containing 2 mM magnesium sulfate), and subjected to 6 cycles of ultrasonic fragmentation each for 15 seconds at an interval of 45 seconds. Thereafter, centrifugation was conducted at 4° C. and 5,500×g for 20 minutes to take the supernatant out and obtain a crude enzyme solution. The crude enzyme solution of each variant enzyme in Table 1 was obtained in the above-described method and used for evaluating the enzyme activity.

<Evaluation of Activity of Crude Enzyme Solution>

(i) Comparison of Ratio T70/T50 of Enzyme Activity (T70) at 70° C. to Enzyme Activity (T50) at 50° C.

The enzyme reaction of the ketose 3-epimerase is an equilibrium reaction and D-psicose:D-fructose=30:70 under an equilibrium condition. For this reason, it is easy to measure the amount of D-fructose generated in the case where D-psicose is used as a substrate. Hence, the evaluation of the activity of the ketose 3-epimerase was conducted by measuring the amount of D-fructose generated in the case where enzyme reaction was caused with D-psicose as a substrate.

Specifically, enzyme reaction was conducted using each crude enzyme solution obtained by the above-described method under reaction conditions shown in Table 2. After the reaction was stopped, the reaction liquid was purified through desalination using an ion-exchange resin, was subjected to filtering, and was loaded to HPLC (HPLC system (manufactured by Tosoh Corporation), MCIGEL CK08EC (manufactured by Mitsubishi Chemical Corporation)). The peak area of D-fructose measured by the HPLC was calculated, and each enzyme activity was calculated from the peak area ratio of 50° C. and 70° C. Here, 1 unit of enzyme activity is defined by the amount of the enzyme which epimerizes D-psicose under each condition to generate 1 μmol of D-fructose in 1 minute. The obtained results are shown in Table 4.

TABLE 2

| Enzyme Reaction Conditions | |
|---|---|
| 0.2M D-psicose (50 mM Phosphoric Acid Buffer (pH 8.0), 2 mM MgSCO$_4$): | 500 μL |
| 50 mM Phosphoric Acid Buffer (pH 8.0), 2 mM MgSCO$_4$): | 400 μL |
| Crude Enzyme Solution: | 100 μL |
| Reaction Temperature: | 50° C. or 70° C. |
| Reaction Time: | Reaction for 10 minutes |
| Reaction Stop Method: | 100° C., 3 minutes |

As a result of the measurement, variant enzymes each having higher T70/T50 than the activity value (0.7±0.1) of the wild type were confirmed from Table 4. It was suggested that these variant enzymes each had improved thermal stability.

As described before, as positions in the specific amino acid sequences which were expected to improve the thermal stability, each position shown in Table 1 was selected to conduct substitution with the amino acid sequences. However, among the created variants, there were variants whose thermal stabilities were not so changed or even lowered, which were unexpected results.

(ii) Comparison of Residual Enzyme Activity A at 50° C. of the Same Enzyme Treated at 60° C. for 1 Hour in 50 mM Phosphoric Acid Buffer (pH 8.0, Containing 2 mM Magnesium Sulfate) Suspension in Case Where Activity at 50° C. of Untreated Enzyme Was Set to 100

Next, the residual activity of the enzyme after heat treatment where the enzyme was left to stand at 60° C. for 1 hour was measured. The enzyme after the heat treatment was reacted using D-psicose as a substrate under conditions shown in Table 3 below using the above obtained crude enzyme solution. After the enzyme reaction was stopped, the reaction liquid cooled down for 10 minutes in an ice water was purified through desalination using an ion-exchange resin and was loaded to the HPLC. The peak area of D-psicose measured by the HPLC was calculated, and the enzyme activities at 50° C. after the heat treatment and of the untreated enzyme were calculated. The residual enzyme activity after the heat treatment was calculated as a relative activity in the case where the untreated enzyme activity was set to 100. The obtained results are shown in Table 4.

TABLE 3

| Heat Treatment Conditions | |
|---|---|
| 50 mM Phosphoric Acid Buffer (pH 8.0), 2 mM MgSCO$_4$): | 400 μL |
| Crude Enzyme Solution (1 mL in total): | 100 μL |
| Heat Treatment Temperature: | 60° C. |
| Heat Treatment Time: | Reaction for 1 hour |
| After Heat Treatment: | Return to Room Temperature |
| Enzyme Reaction Conditions | |
| Reaction Liquid After Heat Treatment: | 500 μL |
| 0.2M D-psicose (50 mM Phosphoric Acid Buffer (pH 8.0), 2 mM MgSCO$_4$): | 500 μL |
| Reaction Temperature: | 50° C. |
| Reaction Time: | Reaction for 10 minutes |
| Reaction Stop Method: | 100° C., 3 minutes |

As a result, variant enzymes each having a residual enzyme activity A exceeding the residual enzyme activity value of the wild-type enzyme were confirmed from Table 4. It was suggested that these enzymes each had a high thermal stability.

TABLE 4

|  | T70/T50 | Residual Enzyme Activity |
|---|---|---|
| Wild Type | 0.7 ± 0.1 | 35.1 |
| PM3 | 0.77 | 37.6 |
| PM4 | 0.82 | 49.8 |
| PM5 | 0.77 | 33.5 |
| PM9 | 0.71 | 29.6 |
| PM12 | 0.77 | 37.5 |
| PM14 | 0.73 | 31.2 |
| PM15 | 0.57 | 29.6 |
| PM17 | 1.25 | 92.9 |
| PM18 | 0.91 | 48.4 |
| PM19 | 0.78 | 22.9 |
| PM23 | 1.52 | 69.9 |
| PM26 | 1.59 | 93.0 |
| PM28 | 0.93 | 22.1 |

TABLE 4-continued

|      | T70/T50 | Residual Enzyme Activity |
|------|---------|--------------------------|
| PM29 | 1.50    | 50.0                     |
| PM31 | 0.73    | 30.9                     |
| PM32 | 1.60    | 100.0                    |
| PM33 | 0.92    | 60.0                     |
| PM36 | 0.47    | 19.1                     |
| PM37 | 0.41    | 25.4                     |
| PM38 | 1.66    | 90.9                     |
| PM39 | 1.01    | 63.2                     |
| PM40 | 0.38    | 22.8                     |
| PM41 | 1.08    | 83.9                     |
| PM43 | 1.41    | 86.0                     |
| PM44 | 0.84    | 52.9                     |
| PM45 | 0.77    | 53.0                     |
| PM46 | 0.76    | 27.6                     |
| PM48 | 0.52    | 46.1                     |
| PM51 | 1.32    | 83.6                     |
| PM55 | 1.24    | 62.9                     |
| PM56 | 0.81    | 33.5                     |
| PM57 | 2.54    | 60.9                     |
| PM58 | 0.90    | 43.7                     |
| PM59 | 0.99    | 20.8                     |
| PM60 | 2.53    | 100.0                    |
| PM61 | 1.67    | 90.8                     |
| PM62 | 0.85    | 30.9                     |
| PM63 | 0.84    | 40.0                     |
| PM64 | 0.92    | 38.4                     |
| PM65 | 1.46    | 86.4                     |

Among the above-described variants, PM3, PM4, PM5, PM9, PM12, PM14, PM17, PM18, PM19, PM23, PM26, PM28, PM29, PM31, PM32, PM33, PM38, PM39, PM41, PM43, PM44, PM45, PM46, PM48, PM51, PM55, PM56, PM57, PM58, PM59, PM60, PM61, PM62, PM63, PM64, and PM65 in particular were more excellent in T70/T50 or residual enzyme activity A than the wild type.

Moreover, among these, PM4, PM17, PM18, PM23, PM26, PM29, PM32, PM33, PM38, PM39, PM41, PM43, PM44, PM45, PM48, PM51, PM55, PM57, PM58, PM60, PM61, PM63, and PM65 in particular each had T70/T50 of 1.0 or more, or the residual enzyme activity A of 40 or more, and were more excellent than the wild type.

Furthermore, PM17, PM23, PM26, PM29, PM32, PM38, PM39, PM41, PM43, PM51, PM57, PM60, PM61, and PM65 each had an activity two times or more the numerical value of T70/T50 or residual enzyme activity A of the wild type and particularly excellent.

<Preparation of Immobilized Enzyme>

1. Crude enzyme solutions of PM38/41/43/51/wild type (hereinafter, WT) were obtained by the same method as that described in <Preparation of Crude Enzyme Solution> described above.

The enzyme activity of each crude enzyme solution was measured using the method and the conditions described in <Evaluation of Activity of Crude Enzyme Solution> and <Table 2> described above.

2. An immobilization carrier (ion-exchange resin AMBER-LITE™ FPA95 or DUOLITE™ A568 (both manufactured by DowDuPont)) equilibrated through washing with a 50 mM phosphate buffer (pH 8.0) containing 2 mM magnesium sulfate and the crude enzyme solution were mixed in a vial in a proportion of an enzyme activity 630U of the crude enzyme solution relative to 1 mL of the immobilization carrier and were mixed by inversion for 24 hours or more.

3. The immobilized enzymes prepared by the above-described method were washed with a 50 mM phosphate buffer (pH 8.0) containing 2 mM magnesium sulfate and stored in a refrigerator of 4° C. until their use.

<Continuous Reaction>

The following experimental procedure was conducted in accordance with JIS K 7002: 1988 (industrial glucose isomerase).

1. 29 mL of the immobilized enzyme was packed in a reactor column (08 mm×L 400 mm) heated to 55° C. and the reaction raw material (containing 50 wt % fructose, 240 ppm of $MgSO_4$, and 150 ppm of $Na_2SO_3$) was loaded into the reactor column.

2. The liquid flowed out of the reactor column was pooled every day and the HPLC analysis (the same method as in <Evaluation of Activity of Crude Enzyme Solution>) was conducted and areas $A_{Psi}$ and $A_{Fru}$ of psicose and fructose in the HPLC chromatogram were calculated.

3. The flow speed of the reaction raw material was adjusted as appropriate such that the isomerization rate x expressed by the equation (1) became 20% or more.

$$x = A_{Psi}/(A_{Psi} + A_{Fru}) \quad (1)$$

4. The enzyme activity "a" of each immobilized enzyme was calculated by the equation (2).

$$a = F/VC_S x_e \ln(x_e/(x_e - x)) \quad (2)$$

where F represents the flow speed of the substrate, $C_S$ represents the concentration of the substrate, $x_e$ represents the apparent equilibrium reaction rate (0.29), and V represents the bed volume of the immobilized enzyme.

Figure 1:
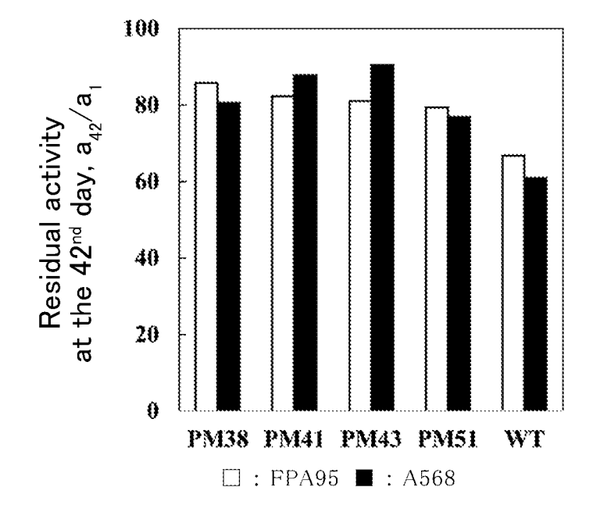
FIG. 1 shows a residual activity of each immobilized enzyme at the 42nd day from the start of operation of a reactor column.

The ratio between the enzyme activity a42 at the 42nd day from the start of operation of the reactor column and the enzyme activity al at the first day from the start of operation (hereinafter, the residual activity at the 42nd day) is shown in FIG. 1 The residual activity of WT at the 42th day was approximately 60%, and the residual activities of PM38/41/43/51 at the 42th day were approximately 80%. Hence, the decrease rate in enzyme activity due to the operation for 42 days was small. This indicates that the decrease in activity is slow.

In the actual production of psicose, the reactor column is often operated for a long period of time (approximately several months to several years) at a temperature of 50° C. or more. In this case, the enzyme activity gradually decreases, so that the amount of psicose produced decreases. The variants presented in Examples are industrially useful because the decrease in activity is slow, so that the amount of psicose produced is also unlikely to decrease.

From the above-described results, the variant enzyme of the present invention makes it possible to efficiently produce D-psicose while maintaining the enzyme activity at the optimum temperature by improving the thermal stability as compared with the conventional wild-type enzymes.

What is claimed is:

1. A variant of ketose 3-epimerase of SEQ ID NO: 1, said variant being selected from the group consisting of PM4, PM17, PM18, PM23, PM26, PM28, PM29, PM32, PM33, PM38, PM39, PM41, PM43, PM44, PM45, PM48, PM51, PM55, PM56, PM57, PM58, PM59, PM60, M61, PM62, PM63, PM64, and PM65, wherein each variant has the following substitution(s) compared to the sequence of SEQ ID NO. 1:

| Ketose 3-epimerase variant | Substitutions in the Amino Acid Sequence of SEQ ID NO: 1 |
| --- | --- |
| PM4 | S137C and N173C |
| PM17 | H271C and D278C |
| PM18 | S67P, D68A, A69D and T70G |
| PM23 | R160A and H289X1 (X1 = VSARHKP (SEQ ID NO: 2)) |
| PM26 | R160A, H271C, D278C and H289X1 (X1 = VSARHKP (SEQ ID NO: 2)) |
| PM28 | S22T, S67P, D68A, A69D, T70G, R160A and H289X1 (X1 = VSARHKP (SEQ ID NO: 2)) |
| PM29 | S22T, S67P, D68A, A69D, T70G, R160A, H177M and H289X2 (X2 = VSARHKP (SEQ ID NO: 2)) |
| PM32 | D278F |
| PM33 | A200L |
| PM38 | V237I |
| PM39 | A200K |
| PM41 | F275C and D278C |
| PM43 | H177M, A200K, V237I, F275C and D278C |
| PM44 | E75P |
| PM45 | T100P and D101V |
| PM48 | R160A and H289X2 (X2 = VSAR (SEQ ID NO: 3)) |
| PM51 | E75P, H177M and V237I |
| PM55 | R160A and H289X3 (X3 = VSARHK (SEQ ID NO: 4)) |
| PM56 | H6Y and H177M |
| PM57 | M110W and H177M |
| PM58 | S67P, A69D and T70G |
| PM59 | S22T and V34I |
| PM60 | D278L |
| PM61 | V237L |
| PM62 | V91I |
| PM63 | A95R |
| PM64 | S137K |
| PM65 | A270K. |

2. The variant of ketose 3-epimerase according to claim 1, which is immobilized on an immobilization carrier.

3. A method for preparing a D-ketose comprising:
treating D-fructose with the variant of ketose 3-epimerase according to claim 1.

4. The variant of ketose 3-epimerase according to claim 1, wherein the variant exhibits
(i) a ketose 3-epimerase enzyme activity at 50° C., higher than that of wild-type ketose 3-epimerase of SEQ ID NO: 1 measured under same condition, wherein the enzyme activity is measured after the variant and the wild-type ketose 3-epimerase are treated at 60° C. for 1 hour in 50 mM phosphate buffer of pH 8.0 and containing 2 mM magnesium sulfate, and/or
(ii) a ratio of the activity at 70° C. (t70) to that at 50° C. (t50), expressed as t70/t50, higher than that of wild-type ketose 3-epimerase of SEQ ID NO: 1.

* * * * *

SEQUENCE LISTING

<160> NUMBER OF SEQ ID NOS: 4

<210> SEQ ID NO 1
<211> LENGTH: 289

```
<212> TYPE: PRT
<213> ORGANISM: Arthrobacter globiformis

<400> SEQUENCE: 1

Met Lys Ile Gly Cys His Gly Leu Val Trp Thr His Phe Asp Ala
1               5                   10                  15

Glu Gly Ile Arg Tyr Ser Val Gln Lys Thr Arg Glu Ala Gly Phe Asp
            20                  25                  30

Leu Val Glu Phe Pro Leu Met Asp Pro Phe Ser Phe Asp Val Gln Thr
                35                  40                  45

Ala Lys Ser Ala Leu Ala Glu His Gly Leu Ala Ala Ser Ala Ser Leu
        50                  55                  60

Gly Leu Ser Asp Ala Thr Asp Val Ser Ser Glu Asp Pro Ala Val Val
65                  70                  75                  80

Lys Ala Gly Glu Glu Leu Leu Asn Arg Ala Val Asp Val Leu Ala Glu
                85                  90                  95

Leu Gly Ala Thr Asp Phe Cys Gly Val Ile Tyr Ser Ala Met Lys Lys
            100                 105                 110

Tyr Met Glu Pro Ala Thr Ala Ala Gly Leu Ala Asn Ser Lys Ala Ala
        115                 120                 125

Val Gly Arg Val Ala Asp Arg Ala Ser Asp Leu Gly Ile Asn Val Ser
    130                 135                 140

Leu Glu Val Val Asn Arg Tyr Glu Thr Asn Val Leu Asn Thr Gly Arg
145                 150                 155                 160

Gln Ala Leu Ala Tyr Leu Glu Glu Leu Asn Arg Pro Asn Leu Gly Ile
                165                 170                 175

His Leu Asp Thr Tyr His Met Asn Ile Glu Glu Ser Asp Met Phe Ser
            180                 185                 190

Pro Ile Leu Asp Thr Ala Glu Ala Leu Arg Tyr Val His Ile Gly Glu
        195                 200                 205

Ser His Arg Gly Tyr Leu Gly Thr Gly Ser Val Asp Phe Asp Thr Phe
    210                 215                 220

Phe Lys Ala Leu Gly Arg Ile Gly Tyr Asp Gly Pro Val Val Phe Glu
225                 230                 235                 240

Ser Phe Ser Ser Ser Val Val Ala Pro Asp Leu Ser Arg Met Leu Gly
                245                 250                 255

Ile Trp Arg Asn Leu Trp Ala Asp Asn Glu Glu Leu Gly Ala His Ala
            260                 265                 270

Asn Ala Phe Ile Arg Asp Lys Leu Thr Ala Ile Lys Thr Ile Glu Leu
        275                 280                 285

His

<210> SEQ ID NO 2
<211> LENGTH: 7
<212> TYPE: PRT
<213> ORGANISM: Artificial sequence
<220> FEATURE:
<223> OTHER INFORMATION: Synthetic construct

<400> SEQUENCE: 2

Val Ser Ala Arg His Lys Pro
1               5

<210> SEQ ID NO 3
<211> LENGTH: 4
<212> TYPE: PRT
<213> ORGANISM: Artificial sequence
```

```
<220> FEATURE:
<223> OTHER INFORMATION: Synthetic construct

<400> SEQUENCE: 3

Val Ser Ala Arg
1

<210> SEQ ID NO 4
<211> LENGTH: 6
<212> TYPE: PRT
<213> ORGANISM: Artificial sequence
<220> FEATURE:
<223> OTHER INFORMATION: Synthetic construct

<400> SEQUENCE: 4

Val Ser Ala Arg His Lys
1               5
```